(12) United States Patent
Rodríguez et al.

(10) Patent No.: US 8,188,440 B2
(45) Date of Patent: May 29, 2012

(54) NEUTRON DOSIMETRY FOR RADIOTHERAPY

(75) Inventors: Faustino Gómez Rodríguez, Santiago (ES); Francisco Miguel Hernandez-Guerra, Concord, CA (US); Alfredo Iglesias Lago, Vedra (ES)

(73) Assignees: Siemens Medical Solutions USA, Inc., Malvern, PA (US); University of Santiago de Compostela (ES)

( * ) Notice: Subject to any disclaimer, the term of this patent is extended or adjusted under 35 U.S.C. 154(b) by 1308 days.

(21) Appl. No.: 11/524,807

(22) Filed: Sep. 20, 2006

(65) Prior Publication Data
US 2010/0258732 A1 Oct. 14, 2010

(51) Int. Cl.
*G01T 3/08* (2006.01)
*G01T 1/02* (2006.01)
(52) U.S. Cl. .............. 250/370.05; 250/390.03
(58) Field of Classification Search ............. 250/370.05, 250/370.01, 370.02, 370.15, 370.04, 390.01, 250/390.04
See application file for complete search history.

(56) References Cited

U.S. PATENT DOCUMENTS

| | | | | |
|---|---|---|---|---|
| 5,498,876 | A * | 3/1996 | Moscovitch | 250/474.1 |
| 6,324,131 | B1 * | 11/2001 | Chen | 369/13.4 |
| 6,552,338 | B1 * | 4/2003 | Doyle | 850/43 |
| 7,220,968 | B2 * | 5/2007 | Burger et al. | 250/370.01 |
| 7,491,948 | B2 * | 2/2009 | Gordon et al. | 250/472.1 |

FOREIGN PATENT DOCUMENTS
EP 1 729 149 A1 6/2006

OTHER PUBLICATIONS

Neutron measurements around medical electron accelerators by active and passive detection techniques, G. Tosi, et al.; Medical Physics 18(1) 1991 54-60.
Characterisation of a gold foil-based Bonner sphere set and measurements of neutron spectra at a medical accelerator, D.J. Thomas et al.; Nuclear Instruments and Methods in Physics Research A 476(2002) 31-35.
Neutron-induced 10B fission as a major source of soft errors in high density SRAMs, R.C. Baumann, et al.; Microelectronics Reliability 41(2002) 211-218.
Monte Carlo study of Siemens PRIMUS photoneutron production, J. Pena, et al; Physics in Medicine and Biology 50(2005) 5921-5933.

* cited by examiner

*Primary Examiner* — David Porta
*Assistant Examiner* — Faye Boosalis (57) ABSTRACT

A system includes emission of a first treatment beam associated with a first energy toward a neutron dose detector, determination of a first number of soft errors experienced by a semiconductor-based device exposed to neutrons generated by the first treatment beam, determination of a first neutron dose based on the first treatment beam using the neutron dose detector, and association of the first energy of the first treatment beam with the first number of soft errors and the first neutron dose. Some aspects include emission of a second treatment beam associated with the first energy toward a target, determination of a second number of soft errors experienced by the semiconductor-based device exposed to neutrons generated by the second treatment beam, and determination of a second neutron dose at the target based on the association between the first energy, the first number of soft errors and the first neutron dose.

33 Claims, 7 Drawing Sheets

| Radiotherapy Room B | | | | | |
|---|---|---|---|---|---|
| MeV | Field | Gantry ∠ | Neutron Dose | SEUs | Conv. Factor |
| 15 | 0 x 0 | 0° | 15 mSv | 1.5 | 10 |
| 15 | 0 x 0 | 90° | 20 mSv | 2.5 | 8 |
| 15 | 10 x 10 | 90° | 38 mSv | 2 | 19 |
| 15 | 20 x 20 | 0° | 120 mSv | 11 | 10.9 |
| 18 | 0 x 0 | 0° | 40 mSv | 2.5 | 16 |
| 18 | 10 x 10 | 90° | 75 mSv | 4 | 18.8 |
| 18 | 20 x 20 | 0° | 200 mSv | 25 | 8 |
| 12 | 0 x 0 | 90° | 10 mSv | 2 | 5 |
| 12 | 20 x 20 | 180° | 50 mSv | 3.5 | 14.3 |

NEUTRON DOSIMETRY FOR RADIOTHERAPY

BACKGROUND

1. Field

The embodiments described below relate generally to radiotherapy. More particularly, some embodiments concern determination of neutron doses resulting from radiation and/or particle therapy.

2. Description

Linear accelerators and particle accelerators generate treatment beams used for patient therapy. At high energies, interactions between a treatment beam and heavy matter within a treatment room (e.g., flattening filters, electron target, collimator, shielding) result in the generation of neutrons. These neutrons may adversely affect a patient to which the treatment beam is delivered. Accordingly, it is desirable to measure neutrons generated within a treatment room.

Conventional active neutron dosimetry devices (e.g., $^3$He proportional counters) are not suitable for the above-mentioned measurement. For example, high energy x-ray leakage fluence generated by a treatment beam is significantly greater than any generated neutron fluence and distorts the measurement thereof. Moreover, high intensity pulsed photon fluences generated by conventional linear accelerators result in neutron counts which correspond to accelerator pulse rates rather than actual neutron fluence. It has been suggested to address the foregoing phenomena by placing active counters outside of a treatment room. Dose determinations based on such placement are not suitably accurate for many applications due to the vague and tenuous relationship between neutron fluence outside a treatment room and neutron dose at a target or other location within the treatment room.

Passive detectors may therefore be employed to detect neutrons generated within a treatment room. Conventional passive detectors include gold foil activation detectors, thermoluminescent dosimeters and superheated bubble emulsions. Each of these passive detectors may be deployed with or without a moderating envelope such as a Bonner sphere. Although passive detectors might not suffer from the above-mentioned deficiencies of active detectors, the time and effort required to analyze a detector after neutron exposure and to determine a neutron dose is unsuitable for efficient verification and/or monitoring of radiotherapy.

SUMMARY

To address at least the foregoing, some embodiments provide a system, method, apparatus, and means to emit a treatment beam toward a target, determine a number of soft errors experienced by a semiconductor-based device exposed to neutrons generated by the treatment beam, and determine a neutron dose at the target based on the determined number of soft errors.

In further aspects, a second treatment beam associated with the first energy is emitted toward a second target, a second number of soft errors experienced by the semiconductor-based device exposed to neutrons generated by the second treatment beam is determined, and a second neutron dose at the second target is determined based on the association between the first energy, the first number of soft errors and the first neutron dose.

Determination of the neutron dose may include determination of the neutron dose based on an association between a beam energy, a first number of soft errors and a first neutron dose at the target. Determination of the neutron dose may also or alternatively include determination of the neutron dose based on an association between a beam energy and a soft errors-to-neutron dose conversion factor.

Some aspects provide emission of a first treatment beam associated with a first energy toward a neutron dose detector, determination of a first number of soft errors experienced by a semiconductor-based device exposed to neutrons generated by the first treatment beam, determination of a first neutron dose based on the first treatment beam using the neutron dose detector, and association of first energy of the first treatment beam with the first number of soft errors and the first neutron dose.

The claims are not limited to the disclosed embodiments, however, as those in the art can readily adapt the description herein to create other embodiments and applications.

BRIEF DESCRIPTION OF THE DRAWINGS

The construction and usage of embodiments will become readily apparent from consideration of the following specification as illustrated in the accompanying drawings, in which like reference numerals designate like parts, and wherein.

DETAILED DESCRIPTION

The following description is provided to enable any person in the art to make and use the described embodiments and sets forth the best mode contemplated by for carrying out some embodiments. Various modifications, however, will remain readily apparent to those in the art.

Figure 1:
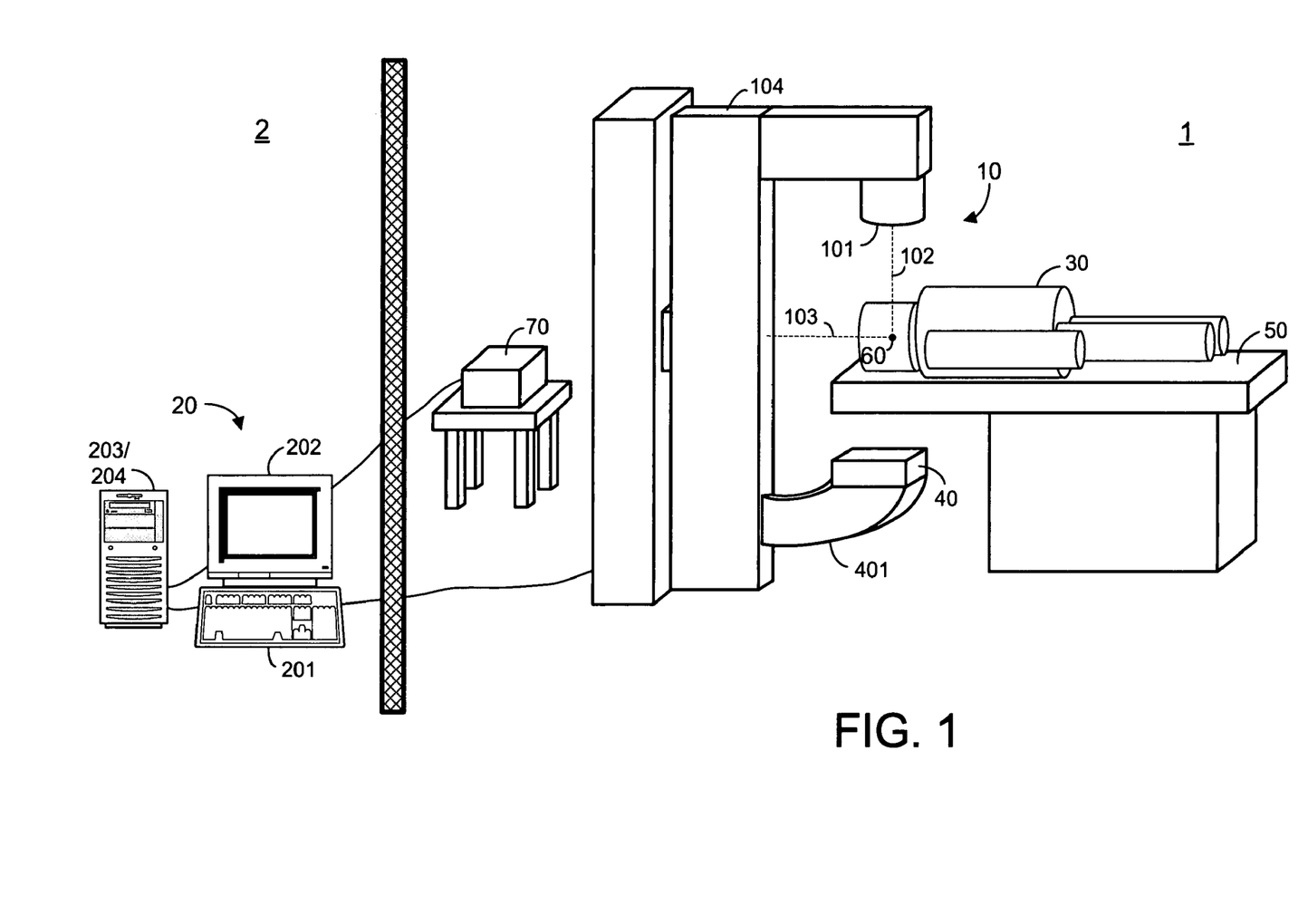
FIG. 1 is a diagram illustrating a radiotherapy system according to some embodiments.

FIG. 1 is a perspective view of treatment room 1 and operator area 2 according to some embodiments. Shown within treatment room 1 are linear accelerator 10, operator console 20, beam object 30, imaging device 40 and table 50. Linear accelerator 10 may be used to generate a high-energy beam for imaging and/or for medical treatment. In this regard, beam object 30 may comprise a patient positioned to receive a beam according to a radiation treatment plan.

Linear accelerator 10 generally delivers a high-energy (e.g., megavoltage) radiation beam from treatment head 101 toward a volume of object 30 located at isocenter 60. Isocenter 60 may be located at an intersection of axis 102 of the aforementioned radiation beam and axis 103 around which gantry 104 is rotatable. According to some embodiments, the radiation beam may comprise photon or electron radiation. Although linear accelerator 10 is shown in FIG. 1, some embodiments are used in conjunction with particle accelerators which deliver a treatment beam composed of particles.

Treatment head 101 includes a beam-emitting device (not shown) for emitting the radiation beam. Also included within treatment head 101 may be a beam-shielding device, or collimator, for shaping the beam and for shielding sensitive surfaces from the beam. Due to characteristic divergence of the radiation beam and the aforementioned shaping of the beam, the radiation beam delivers radiation to a radiation field rather than only to isocenter 60. An accessory tray may be mounted on treatment head 101 and configured to receive and securely hold attachments used during the course of treatment planning and treatment. These attachments may include an array of beam-attenuating elements, reticles, wedges, filters and/or apertures.

Imaging device 40 may acquire an image based on received photon radiation (i.e., X-rays) and/or electron radiation. The images may be acquired before, during and after radiation treatment. For example, imaging device 40 may acquire images for diagnosis, verification and recordation of a patient position, and verification and recordation of an internal patient portal to which treatment radiation is delivered. The effectiveness of radiation treatment often depends on the quality of these acquired images.

Imaging device 40 may be attached to gantry 104 in any manner, including via extendible and retractable housing 401. Rotation of gantry 104 may cause treatment head 101 and imaging device 40 to rotate around the isocenter such that isocenter 60 remains located between treatment head 101 and imaging device 40 during the rotation.

Table 50 supports object 30 during image acquisition and/or radiation therapy. Table 50 is adjustable to ensure, along with rotation of gantry 104, that a volume of interest is positioned between treatment head 101 and imaging device 40. Table 50 may also be used to support devices used for acquisition of correction images, other calibration tasks and/or beam verification.

In operation, interactions between an emitted beam and the elements of treatment head 101 may result in the generation of neutrons via well-known physical phenomena. For example, a megavoltage treatment beam may generate fast neutrons having energies of 0.8 to 1 MeV. However, interactions of these fast neutrons with the elements and walls of treatment room 1 may result in a field of low energy neutrons (i.e., epithermal and thermal) within treatment room 1.

Semiconductor-based device 70 is located in treatment room 1 along with linear accelerator 10. According to some embodiments, semiconductor-based device 70 is exposed to neutrons generated by a treatment beam emitted from linear accelerator 10. The neutrons to which semiconductor-based device 70 is exposed may comprise any of the epithermal, thermal and fast neutrons described above.

Semiconductor-based device 70 may experience soft errors due to the neutron exposure. Soft errors are events caused by particles passing through an electronic device and producing an ionization charge sufficient to affect the electronic device. A single-event upset (SEU) is a soft error such as a flipped bit within a memory location. This type of SEU is detectable by reading the memory location and comparing the value with an expected value. In addition, this SEU is reversible simply by re-writing to the impacted memory location.

Semiconductor-based device 70 may comprise any element or combination of elements in which soft errors occur due to neutron exposure. Moreover, semiconductor-based device 70 may comprise any element or combination of elements from which the number of soft errors may be determined. Semiconductor-based device 70 may comprise one or more static random access memories (SRAMs), dynamic random access memories, flash memories, microprocessors, and field-programmable gate arrays, but embodiments are not limited thereto.

In some embodiments, device 70 comprises an SRAM including sub-micron features and a Boro-Phosphate-Silicate-Glass layer. Device 70 may be particularly susceptible to soft errors caused by thermal neutrons (i.e., below 1 eV). Device 70 may be placed such that it cannot be directly reached by a beam emitted from treatment head 101. According to some embodiments, device 70 is surrounded by a moderator material (e.g., polyethylene) to increase the effect of fast neutrons within treatment room 1 on a number of soft errors experienced by device 70. In some embodiments, a nominal voltage of device 70 may be reduced to reduce a charge threshold of a memory element and to thereby increase a susceptibility of device 70 to neutron-caused soft errors.

Operator area 2 is separated from treatment room 1 by wall 3 and includes operator console 20. Wall 3 may therefore protect an operator from radiation emitted by linear accelerator 10. For example, accelerator 10 may be located in a heavily shielded room, such as a concrete vault, which shields the operator from the emitted treatment beam as well as from the electromagnetic and neutron fields resulting therefrom.

Operator console 20 may control linear accelerator 10 and interface with device 70 according to some embodiments. Specifically, operator console 20 may control accelerator 20 to emit a treatment beam toward a target and may communicate with device 70 to determine a number of soft errors experienced by device 70 as a result of exposure to neutrons generated by the treatment beam. Operator console 20 may also determine a neutron dose at the target based on the determined number of soft errors.

Input device 201 of operator console 20 may receive instructions from an operator such as an instruction to deliver treatment radiation according to a treatment plan. Console 20 also includes output device 202; which may be a monitor for presenting an indication of a neutron dose at a target, operational parameters of linear accelerator 10 and/or interfaces for controlling elements 10, 40 and/or 50. Output device 202 may also present images acquired by imaging device 40. Input device 201 and output device 204 are coupled to processor 203 and storage 204.

Processor 203 executes program code according to some embodiments. The program code may be executable to control elements of room 1 to operate as described herein. The program code may be stored in storage 204, which may comprise one or more storage media of identical or different types, including but not limited to a fixed disk, a floppy disk, a CD-ROM, a DVD-ROM, a Zip™ disk, a magnetic tape, and a signal. Storage 204 may, for example, store calibration tables, radiation treatment plans, portal images, software applications to calibrate elements of system 1 and/or to provide radiation treatment, and other data used to perform radiation treatment.

According to some embodiments, the above-mentioned program code may be executed to emit a treatment beam toward a target, to determine a number of soft errors experienced by semiconductor-based device 70 exposed to neutrons generated by the treatment beam, and to determine a neutron dose at the target based on the determined number of soft errors. The program code may further be executed to emit a second treatment beam associated with the first energy toward a second target, determine a second number of soft errors experienced by the semiconductor-based device exposed to neutrons generated by the second treatment beam, and determine a second neutron dose at the second target based on the association between the first energy, the first number of soft errors and the first neutron dose. Some embodiments of the foregoing will be described in detail below.

Each of the devices shown in FIG. 1 may include less or more components than those shown. In addition, embodiments are not limited to the components shown in FIG. 1.

Figure 2:
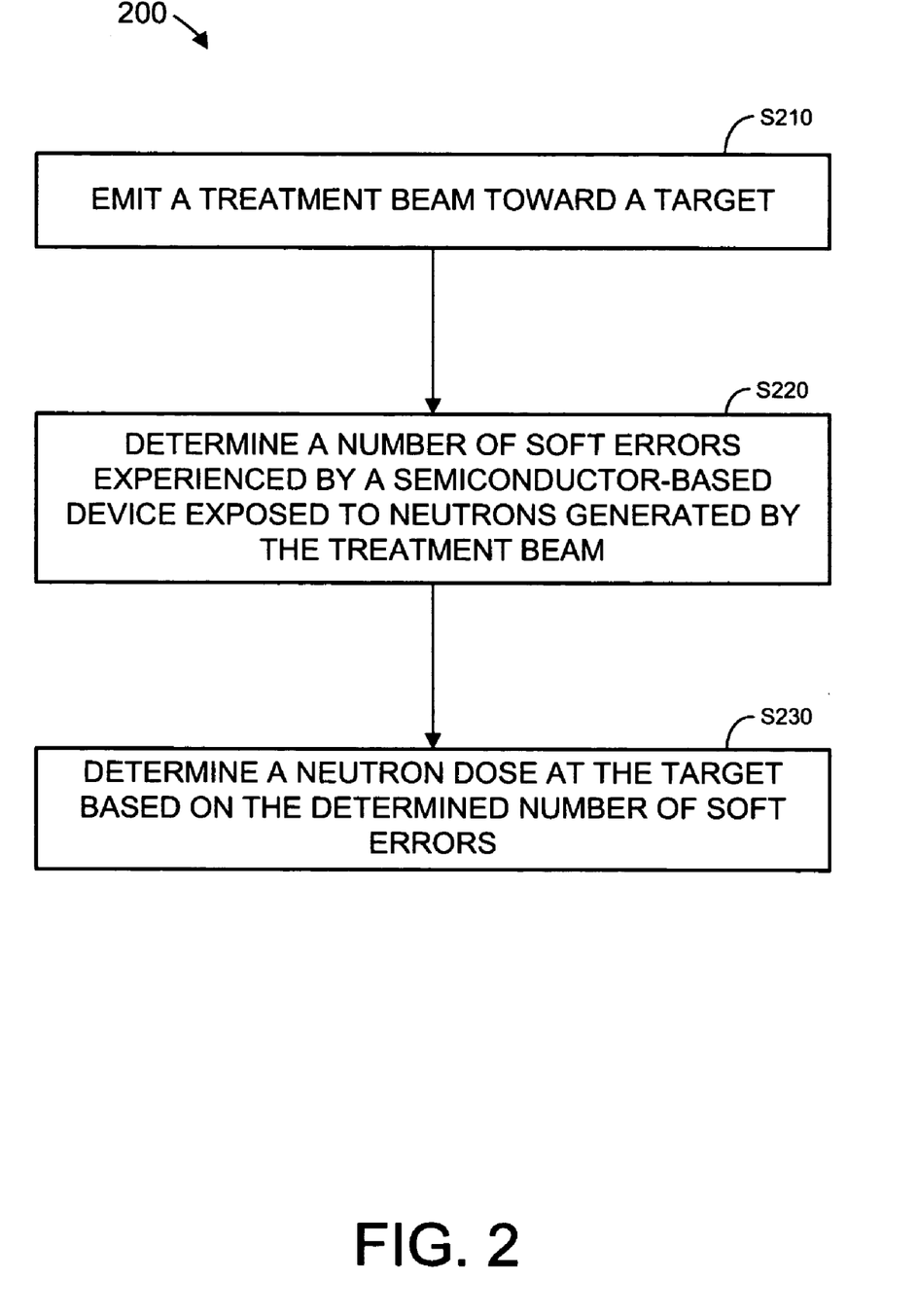
FIG. 2 comprises a flow diagram of process steps according to some embodiments.

FIG. 2 is a flow diagram of process steps 200 according to some embodiments. Process steps 200 and other process steps described herein may be embodied, in whole or in part, by hardware of and/or software executed by elements including but not limited to those of accelerator 10, device 70 and operator console 20. Software embodying these process steps may be stored by any medium residing in any suitable device, including a fixed disk, a floppy disk, a CD-ROM, a DVD-ROM, a Zip™ disk, a magnetic tape, or a signal. Some or all of such software may also be stored in one or more devices.

Initially, at S210, a treatment beam is emitted toward a target. According to some embodiments of S210, operator console 20 issues a command to linear accelerator 10 to emit a treatment beam toward isocenter 60. The treatment beam may be filtered and/or shaped by any suitable devices of treatment head 101. As mentioned above, interactions between the beam and the devices of treatment head 101 may generate fast neutrons. Epithermal and thermal neutrons may then result from scattering of the fast neutrons within room 1.

Next, at S220, a number of soft errors is determined. The soft errors comprise errors experienced by a semiconductor-based device that is exposed to neutrons generated by the treatment beam. In some embodiments, the soft errors comprise SEUs experienced by an SRAM. Operator console 20 may determine the number of soft errors by reading memory locations of the SRAM and by comparing the read values with expected values. According to some embodiments, semiconductor-based device 70 includes one or more SRAMs as well as logic and buffers to determine the number of soft errors experienced by the SRAMs.

A neutron dose at the target is determined at S230 based on the determined number of soft errors. The neutron dose is determined, according to some embodiments, based on an association between a beam energy, a first number of soft errors and a first neutron dose at the target. Examples of such an association are provided below. In some embodiments, the neutron dose is determined based on an association between a beam energy and a soft errors-to-neutron dose conversion factor.

Embodiments of process steps 200 may provide efficient determination of a neutron dose delivered to a radiotherapy target.

Figure 3:
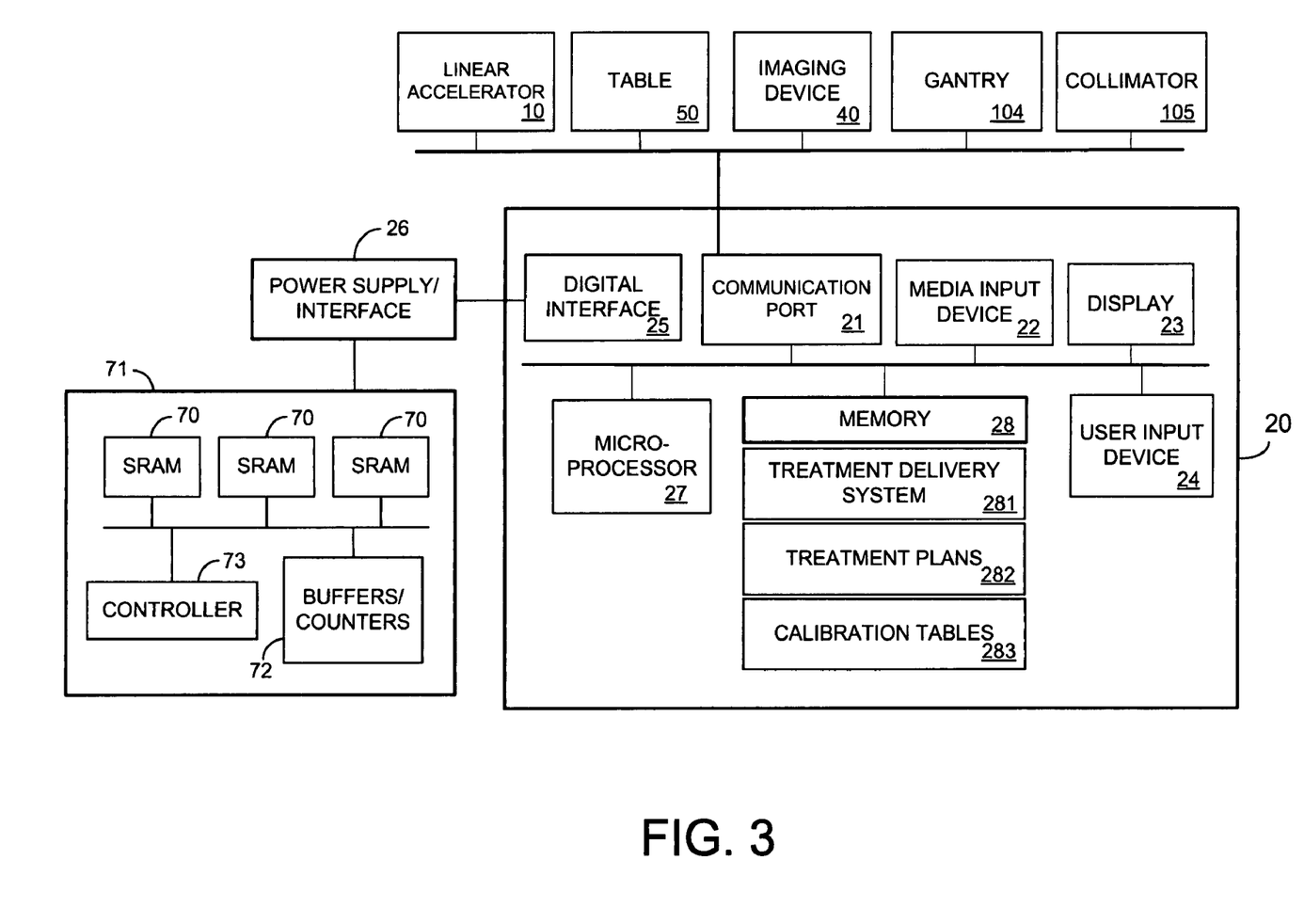
FIG. 3 is a block diagram illustrating elements of a radiotherapy system according to some embodiments.

FIG. 3 is a block diagram including some elements of FIG. 1 according to some embodiments. The illustrated blocks may be implemented by any suitable combination of hardware, software and/or firmware. Some embodiments differ partially or completely from that shown in FIG. 3.

Operator console 20 of FIG. 3 includes communication port 21 for interfacing with external elements. Operator console 20, may, for example, issue a command over communication port 21 to control linear accelerator 10 to emit a radiation beam having a particular energy. Operator console 20, may issue other commands over communication port 21 to move table 50, to acquire a portal image via imaging device 40, to rotate gantry 104, and to configure collimator 105 to produce a particular field size at isocenter 60.

Communication port 21 may comprise any type of interface suitable for receiving data from operator console 20. Communication port 21 may comprise a proprietary interface associated with a manufacturer of linear accelerator 10. Operator console 20 also includes media input device 22 that may comprise a CD-ROM drive, a ZIP drive, a USB drive and/or any device for receiving a storage medium and reading data and/or program code from the medium.

In some embodiments, operator console 20 also includes digital interface 25 for communicating with external power supply/interface 26. Digital interface 25 may comprise an RS485 or an LVDS interface according to some embodiments. Power supply/interface 26 may be located in treatment room 1 and may include +5 V digital interface components and a variable power supply for SRAMs 70 of detector board 71.

The embodiment differs from the embodiment of FIG. 1 in that detector board 71 may reside in room 1 and may determine the number of soft errors experienced by device 70. Detector board 71 according to some embodiments includes buffers/counters 72 and controller 73 (e.g., a fused field-programmable gate array). Buffers/counters 72 and controller 73 may operate to determine a number of soft errors experienced by SRAMs 70. Elements 72 and 73 may be radiation-hardened in view of the fields to which detector board 71 will be exposed within treatment room 1. In some embodiments, however, elements 72 and 73 operate primarily before and after emission of a treatment beam to write and read, respectively, SRAMs 70. Accordingly, the fields may not significantly compromise operation of elements 72 and 73.

Operator console 20 and detector board 71 may be integrated with one another to any degree in order to provide the functions described herein. In some embodiments, detector board 71 is not coupled to operator console 20. Operator console 20 may operate to control linear accelerator 10 and detector board 71 may separately operate in conjunction with SRAMs 70 to determine soft errors.

Microprocessor 27 executes processor-executable program code stored in memory 28 to provide operation according to some embodiments. In this regard, memory 28 may program code that is executable by microprocessor 27. This program code may comprise treatment delivery system 281 to provide treatment delivery according to treatment plans 282 and to provide operation as described herein. Memory 28 may also comprise calibration tables 283 to calibrate linear accelerator 10 and detector board 71. In some embodiments, calibration tables 283 associate beam energies with soft errors and neutron doses and may be used to determine a neutron dose. Examples and usage of calibration tables 283 according to some embodiments will be described below.

Figure 4:
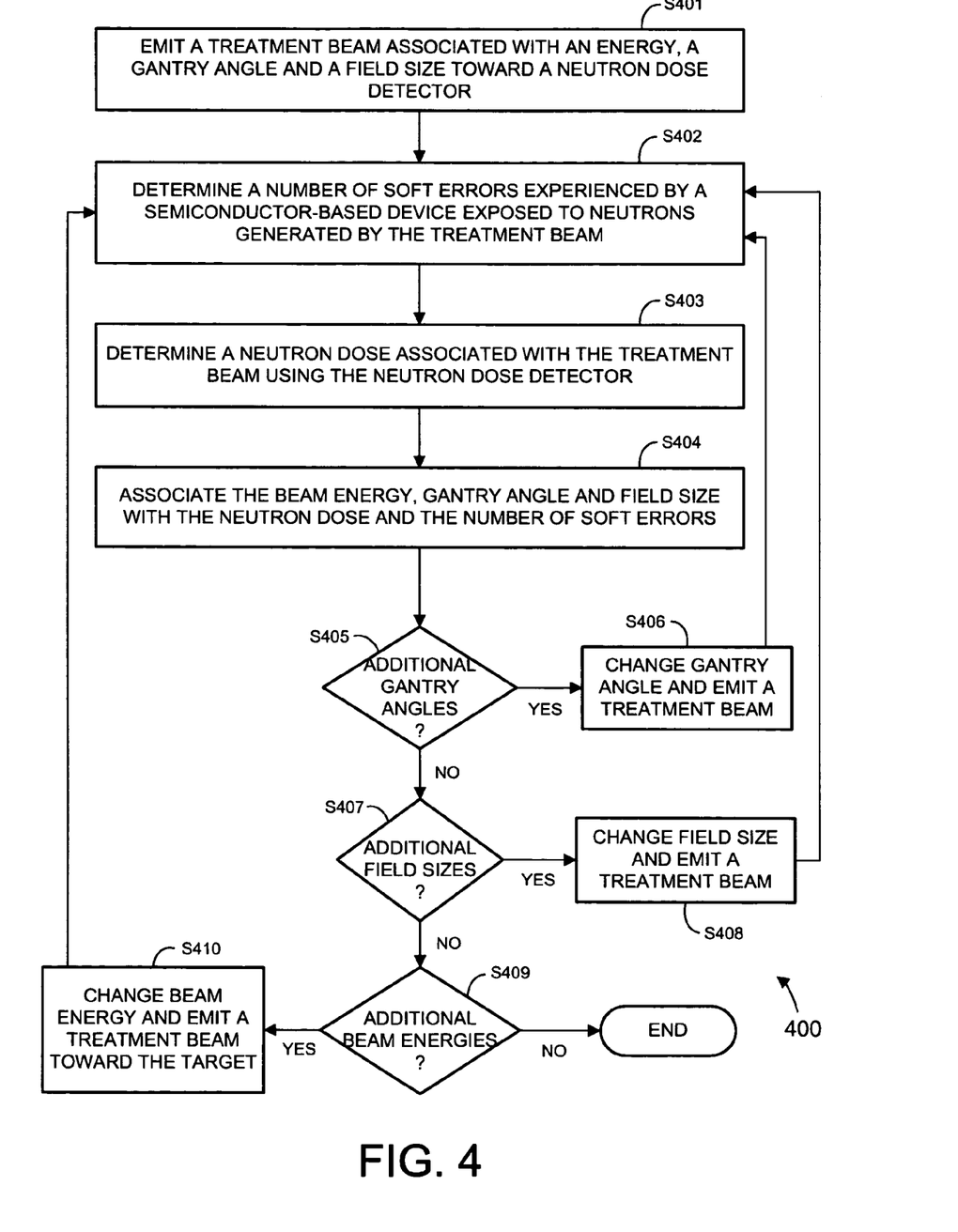
FIG. 4 comprises a flow diagram of process steps according to some embodiments.

FIG. 4 is a flow diagram of process steps 400 to associate beam energies, soft errors and neutron doses according to some embodiments. The associations may be used as described herein to determine a neutron dose at a target, an isocenter, or at another location within a treatment room. Process steps 400 may be performed during calibration and/or quality assurance.

A treatment beam is emitted toward a neutron dose detector at S401. The treatment beam is associated with an energy, a gantry angle and a field size. According to some embodiments, the neutron dose detector comprises a passive neutron detector located within a phantom.

Figure 5:
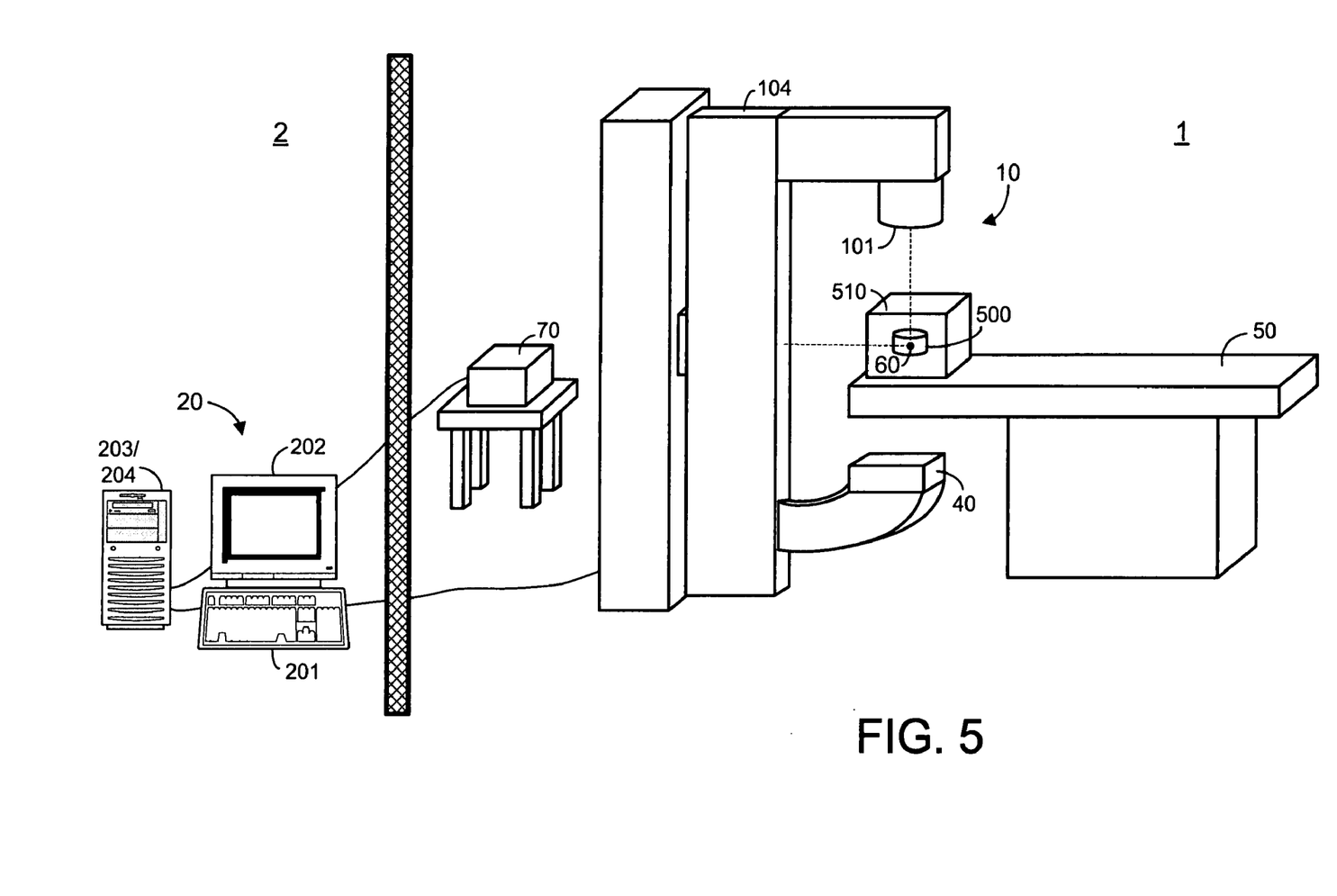
FIG. 5 is a diagram illustrating a radiotherapy system according to some embodiments.

FIG. 5 illustrates treatment room 1 according to some embodiments of S401. Neutron dose detector 500 is disposed within phantom 510 and isocenter 60 of linear accelerator 10 is located within detector 500. Phantom 510 may comprise any suitable dimensions and composition. In some embodiments, phantom 510 comprises a water-filled or otherwise tissue-equivalent volume to simulate a patient volume. Accordingly, irradiation of phantom 510 may generate neutron fields similar to those generated during irradiation of a patient volume.

Detector 500 may comprise any suitable neutron dose detector, including but not limited to gold foil activation detectors, thermoluminescent dosimeters and superheated bubble emulsions. Detector 500 may be located at any position within the treatment beam, including positions away from isocenter 60, according to some embodiments of S401. The location of detector 500 at S401 determines the location at which a neutron dose will be determined during subsequent radiotherapy according to some embodiments.

The treatment beam energy, gantry angle and field size used at S401 may comprise any values for which an association is desired. Referring to FIG. 3, microprocessor 25 of operator console 20 may execute program code of treatment delivery system 281 to control linear accelerator 10 to emit a beam of the desired energy, to control gantry 104 to rotate to the desired angle, and to control collimator 105 to shape the divergent beam to the desired field size.

A number of soft errors is determined at S402 after emission of the treatment beam. The soft errors comprise errors experienced by a semiconductor-based device that is exposed to neutrons generated by the emitted treatment beam.

According to some embodiments, microprocessor 27 of operator console 20 executes program code to check a connection between digital interface 25, interface 26 and detector board 71 prior to S401. Next, and also prior to S401, detector board 71 is instructed to write a known data pattern to SRAMs 70. The written data pattern may be selected by an operator and/or may be verified by detector board 71 and/or operator console 20 according to some embodiments. S402 may then comprise reading data from SRAMs 70 and determining the number of soft errors by comparing the read data with the written data. In some embodiments such as that illustrated in FIG. 5, operator console 20 is coupled directly to semiconductor-based device 70 and performs the foregoing steps without using detector board 71.

A neutron dose associated with the treatment beam is determined at S403 using the neutron dose detector. Some embodiments may utilize any neutron dose detector and system for reading a dose therefrom. As mentioned above, some systems for determining neutron doses may require significant time and resources.

Figure 6:
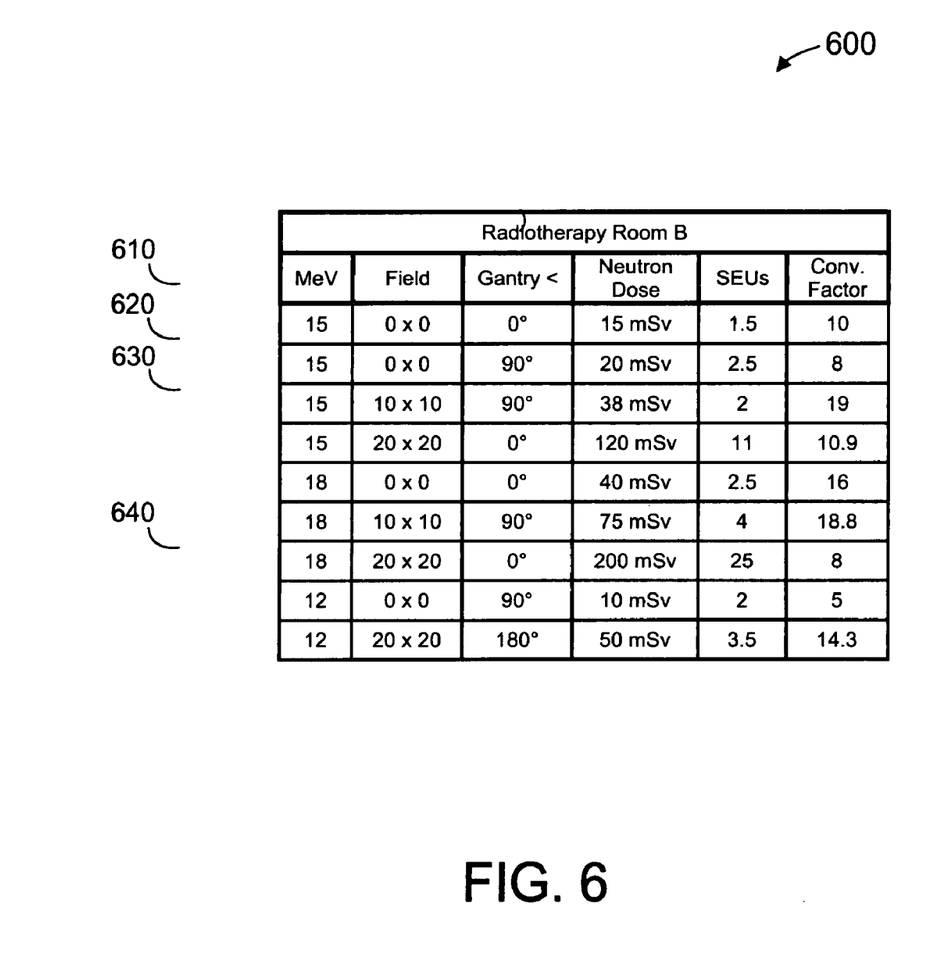
FIG. 6 is a tabular representation of associations between beam energies, soft errors and neutron doses according to some embodiments.

Next, at S404, the beam energy, gantry angle and field size used to emit the beam at S401 are associated with the determined neutron dose and the determined number of soft errors. FIG. 6 is a tabular representation of a portion 600 of calibration tables 283 to illustrate the association of S404. As shown, the beam energy, gantry angle and field size may be associated with the neutron dose and the number of soft errors by storing each of these values in a data record. S404 may comprise any other technique for creating an association between several values.

Each record of portion 600 associates a beam energy, a field size, and a gantry angle with a neutron dose and a number of soft errors (e.g., SEUs). Each record also includes a conversion factor computed based on the neutron dose and a number of soft errors. The conversion factor may facilitate conversion of a number of soft errors occurring at a first location within a treatment room to a neutron dose received at a second location within the treatment room. Portion 600 may include more or fewer fields than shown in FIG. 6.

As shown, portion 600 is associated with a specific radiotherapy room. Generation of epithermal and thermal neutrons is highly dependent on room dimensions, wall composition, equipment layout, etc. Therefore, associations created according to some embodiments of S404 are room-specific.

Returning to process steps 400, it is determined at S405 whether data for additional gantry angles is desired. An operator may manually specify desired gantry angles and/or the desired gantry angles may be hard-coded into program code executed by microprocessor 27. If additional gantry angles are desired, the gantry angle is changed and a new treatment beam is emitted at S406.

S402 through S404 are repeated as described above with respect to soft errors and neutron doses caused by the new treatment beam. According to the present example, a new record of portion 600 is created at S404 including the same beam energy and field size as the previously-created record, but reflecting the changed gantry angle and newly-determined soft errors and neutron dose. The foregoing relationship is reflected by records 610 and 620.

If the determination at S404 is negative, it is determined at S407 whether data for additional field sizes is desired. If so, the field size is changed and a new treatment beam is emitted at S406. Collimator 105 may be controlled to change the field size in some embodiments. Again, S402 through S404 are repeated as described above with respect to soft errors and neutron doses caused by the new treatment beam. Record 630 of portion 600 reflects a new association created at S404 in view of the changed field size.

Flow proceeds from S407 to S409 if the determination at S407 is negative. If it is determined at S409 that data for additional beam energies field sizes is desired, the beam energy is changed and a new treatment beam is emitted at S410. Upon returning to S404, the new beam energy and current field size and gantry angle are associated with soft errors and neutron doses caused by the new treatment beam. In the present example, record 640 is created at S404.

Embodiments for associating one or more beam energies with one or more gantry angles, one or more field sizes, one or more neutron doses, and one or more numbers of soft errors may differ from process steps 400.

Figure 7:
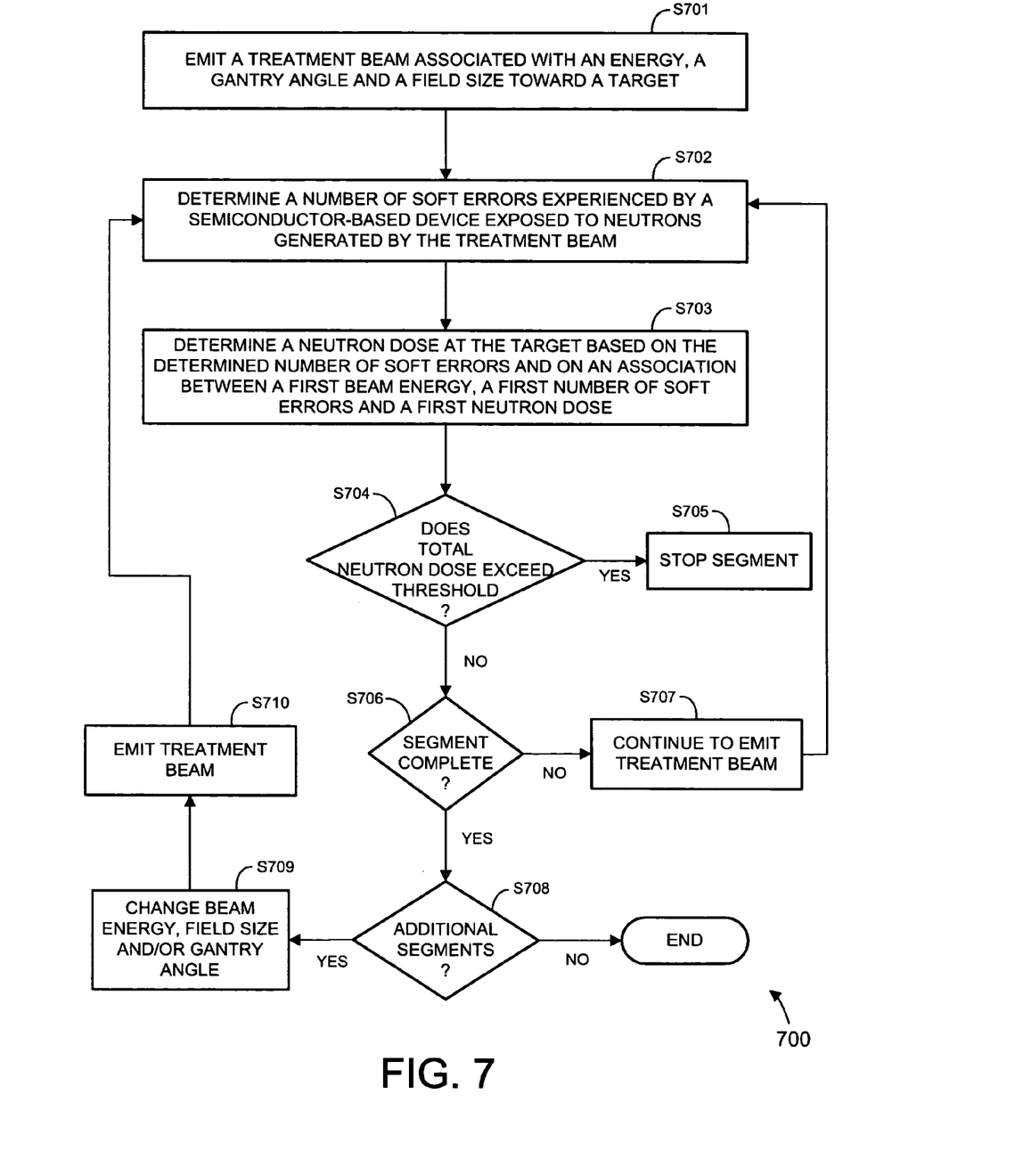
FIG. 7 comprises a flow diagram of process steps according to some embodiments.

FIG. 7 is a flow diagram of process steps 700 according to some embodiments. Process steps 700 may be performed to determine a neutron dose at a location within a treatment room based on a number of soft errors occurring at another location within the treatment room. Examples of process steps 700 are provided below with respect to the elements of FIG. 1 and FIG. 3 but embodiments are not limited thereto.

A treatment beam is emitted toward a target at S701. The treatment beam is associated with an energy, a gantry angle and a field size. The treatment beam energy, gantry angle and field size may comprise any desired values. According to some embodiments of S701, the energy, gantry angle, field size and other characteristics of the treatment beam are specified by a multi-segment treatment plan of treatment plans 282. Treatment delivery system 281 is therefore executed to control linear accelerator 10, gantry 104e, and collimator 105 according to a first segment of the treatment plan.

The target toward which the treatment beam is emitted may comprise an internal volume of a patient. The target may or may not be located at isocenter 60 of linear accelerator 10. Accordingly, the subsequently-determined neutron dose may or not correspond to a dose received at isocenter 60.

A number of soft errors is determined at S702. The soft errors comprise errors experienced by a semiconductor-based device that is exposed to neutrons generated by the emitted treatment beam. As described above, a known data pattern may be stored in SRAM 70 of FIG. 1 prior to S701. S702 may therefore comprise reading data from SRAM 70 and determining the number of soft errors by comparing the read data with the stored data. S702 may be performed by on-board devices such as controller 73 and buffers/counters 72 of detector board 71, and/or by operator console 20.

A neutron dose at the target is determined at S703. The neutron dose is determined based on the determined number of soft errors and on an association between a beam energy, a first number of soft errors and a first neutron dose. Such an association is provided by each record of tabular portion 600. According to some embodiments of S703, a record of tabular portion 600 is identified which specifies the beam energy, field size and gantry angle of the emitted treatment beam. The neutron dose may then be determined based on the neutron dose specified in the record, the SEUs specified in the record, and the number of soft errors determined at S702. In some embodiments of S703, the determined number of soft errors is multiplied by the conversion factor of the record to determine the neutron dose.

In accordance with the previous example, the association used at S703 corresponds to the radiotherapy room in which the treatment beam is being emitted. Process steps 400 may therefore be performed prior to process steps 700 within a radiotherapy room. Moreover, several associations (e.g., records of tabular portion 600) may be used at S703 to determine the neutron dose received at the target. For example, values of two or more records may be interpolated if no single record specifies the particular energy, field size, and/or gantry angle of the beam emitted at S701.

The neutron dose determined at S703 may comprise a dose equivalent calculated using a neutron energy spectrum. In this regard, the first neutron dose described at S703 may comprise several doses corresponding to certain energy spectrum intervals of the neutron fluence that may be stored in association with a number of SEUs and a beam energy within portion 600. The dose equivalent may also be determined based on a single dose value obtained as described above, and on known relationships between the absorption of neutrons of different energies within tissue, the neutron energy spectrum at a certain target location and the corresponding measurements of the neutron detector used to generate the dose values of portion 600. The neutron energy spectrum may be obtained through measurements or calculated by simulation (e.g., Monte Carlo).

The first neutron dose used at S703 may have been detected by a neutron dose detector located at a position other than isocenter 60 of linear accelerator 10. The neutron dose determined at S703 may therefore correspond to a neutron dose received at the position at which the neutron dose detector was located rather than at isocenter 60.

At S704, it is determined whether a total neutron dose exceeds a threshold. The total neutron dose may comprise a total of all neutron doses determined since a commencement of process steps 700. The threshold may be user-specified and/or hard-coded, and may comply with safety recommendations of an authoritative body.

The executing treatment plan segment is stopped at S705 if the total neutron dose exceeds the threshold. According to some embodiments, linear accelerator 10 continues to emit the treatment beam during S702 through S704. Flow proceeds to S706 from S704 if the total neutron dose does not exceed the threshold.

S706 comprises a determination of whether the segment is complete. If not, flow proceeds to S707 for continued emission of the treatment beam. S707 may be unnecessary if linear accelerator 10 continues to emit the treatment beam during S702 through S706. Flow then returns to S702 and S703 to newly-determine a number of soft errors and a neutron dose as described above. The total neutron dose evaluated at S704 therefore includes both the previously-determined and the newly-determined neutron dose.

Flow continues to S708 from S706 if the segment is complete. If additional segments are identified at S708, the beam energy, field size and/or gantry angle are changed at S709 based on criteria specified by a next treatment plan segment. A new beam is emitted at S710 and flow returns to S702 as described above.

A predetermined amount of time may pass between S710 and S702, between S707 and S702, and between S701 and S702 to allow for the accumulation of soft errors by the semiconductor-based device. Also, some embodiments comprise resetting the stored data pattern within the semiconductor-based device after each execution of S702.

Process steps 700 terminate once it is determined at S708 that no additional segments remain. Accordingly, process steps 700 may provide efficient monitoring of a neutron dose received at a target during multi-segment radiotherapy.

Some embodiments may operate to measure the damage/risk due to radiation by determining a dose equivalent and/or an effective dose. As alluded to above, a dose equivalent may be calculated by determining a neutron dose as described above, separating the dose according to energy spectrum levels, and applying to each separated spectrum level different dimensional weighting factors that depend on the neutron energy. Moreover, an effective dose can be obtained by multiplying the dose equivalent associated with each organ by a weighting factor associated with the organ and by summing the resulting products.

Calculation of a dose equivalent and/or an effective dose may be particularly suitable in a case that a gantry orientation and a field size (i.e., collimator position) are unknown. Such a scenario may occur in a case that a semiconductor-based device and associated circuitry (e.g., detector board 71) are not in communication with the beam-emitting device. In some embodiments of the foregoing, a neutron dose is determined based on the beam energy, a number of soft errors experienced by the semiconductor-based device, and on data associating a first number of soft errors and a first beam energy with a neutron dose. A maximum dose equivalent and/or effective dose may be determined from the neutron dose and may be used by clinical staff to judge the risk of the associated radiotherapy therapy (e.g., multi-segment therapy such as Intensity Modulated Radiation Therapy).

Those in the art will appreciate that various adaptations and modifications of the above-described embodiments can be configured without departing from the scope and spirit of the claims. Therefore, it is to be understood that the claims may be practiced other than as specifically described herein.

What is claimed is:

1. A method comprising:
   emitting, by an accelerator located in a treatment room, a treatment beam toward a target located at a first location within the treatment room;
   determining a number of soft errors experienced by a semiconductor-based device located in the treatment room at a second location and exposed to neutrons generated by the treatment beam, the first location and the second location being different locations; and
   determining a neutron dose at the target located at the first location based on the determined number of soft errors experienced by the semiconductor-based device located at the second location and characteristics of the treatment room.

2. A method according to claim 1, wherein the soft errors comprise single-event upsets.

3. A method according to claim 1, wherein the semiconductor-based device located at the second location is not directly reached by the emitted treatment beam.

4. A method according to claim 1, wherein determining the neutron dose comprises:

determining the neutron dose based on an association between a beam energy, a first number of soft errors and a first neutron dose at the target.

5. A method according to claim 4, wherein the association further associates the beam energy with a second number of soft errors and a second neutron dose at the target.

6. A method according to claim 4, wherein determining the neutron dose comprises:
determining the neutron dose based on an association between a beam energy and a soft errors-to-neutron dose conversion factor.

7. A method according to claim 4, wherein the treatment beam is associated with the beam energy and a field size, and
wherein the association associates the beam energy and the field size with the first number of soft errors and the first neutron dose at the target.

8. A method according to claim 1, wherein determining the neutron dose comprises:
determining that the number of soft errors exceeds a threshold associated with a threshold neutron dose.

9. A method according to claim 1, further comprising:
determining a dose equivalent based on the neutron dose.

10. A method according to claim 9, further comprising:
determining an effective dose based on the dose equivalent.

11. A system comprising:
a beam source located in a treatment room to emit a treatment beam toward a target located at a first location within the treatment room;
a semiconductor-based device located in the treatment room at a second location to experience soft errors due at least in part to neutrons generated by the treatment beam, the first location and the second location being different locations; and
a processor to determine a number of soft errors experienced by the semiconductor-based device located at the second location, and to determine a neutron dose at the target located at the first location based on the determined number of soft errors experienced by the semiconductor-based device located at the second location and characteristics of the treatment room.

12. A system according to claim 11, wherein the soft errors comprise single-event upsets.

13. A system according to claim 11, wherein the semiconductor-based device located at the second location is not directly reached by the emitted treatment beam.

14. A system according to claim 11, wherein the processor is to determine the neutron dose by:
determining the neutron dose based on an association between a beam energy, a first number of soft errors and a first neutron dose at the target.

15. A system according to claim 14, wherein the processor is to determine the neutron dose by:
determining the neutron dose based on an associating between a beam energy and a soft errors-to-neutron dose conversion factor.

16. A system according to claim 14, wherein the treatment beam is associated with the beam energy and a field size, and
wherein the association associates the beam energy and the field size with the first number of soft errors and the first neutron dose at the target.

17. A system according to claim 11, wherein the processor is to determine the neutron dose by:
determining that the number of soft errors exceeds a threshold associated with a threshold neutron dose.

18. A system according to claim 11, wherein the processor is to determine a dose equivalent based on the neutron dose.

19. A system according to claim 18, wherein the processor is to determine an effective dose based on the dose equivalent.

20. A method comprising:
emitting, in a treatment room, a first treatment beam associated with a first energy toward a neutron dose detector located at a first location;
determining a first number of soft errors experienced by a semiconductor-based device located in the treatment room at a second location and exposed to neutrons generated by the first treatment beam the first location and the second location being different locations;
determining a first neutron dose based on the first treatment beam using the neutron dose detector located at the first location; and
associating the first energy of the first treatment beam with the first number of soft errors experienced by the semiconductor-based device located at the second location, the first neutron dose, and characteristics of the treatment room.

21. A method according to claim 20, wherein the soft errors comprise single-event upsets.

22. A method according to claim 20, further comprising:
emitting a second treatment beam associated with a second energy toward the detector located at the first location;
determining a second number of soft errors experienced by the semiconductor-based device located at the second location and exposed to neutrons generated by the second treatment beam;
determining a second neutron dose based on the second treatment beam using the neutron dose detector located at the first location; and
associating the second energy of the second treatment beam with the second number of soft errors experienced by the semiconductor-based device located at the second location and the second neutron dose.

23. A method according to claim 20, wherein the first treatment beam is associated with a first field size, and
wherein the associating comprises associating the first energy of the first treatment beam and the first field size with the first number of soft errors and the first neutron dose.

24. A method according to claim 20, further comprising:
emitting a second treatment beam associated with the first energy toward a target;
determining a second number of soft errors experienced by the semiconductor-based device exposed to neutrons generated by the second treatment beam; and
determining a second neutron dose at the target based on the association between the first energy, the first number of soft errors and the first neutron dose.

25. A method according to claim 24, wherein the target comprises an internal patient volume.

26. A method according to claim 25, wherein determining the second neutron dose comprises:
determining that the second number of soft errors exceeds a threshold associated with a threshold neutron dose.

27. A system comprising:
a neutron dose detector located in a treatment room at a first location;
a beam source located in the treatment room to emit a first treatment beam associated with a first energy toward the neutron dose detector located at the first location;
a semiconductor-based device located in the treatment room at a second location to experience a first number of soft errors due, at least in part, to neutrons generated by the first treatment beam, the first location and the second location being different locations; and a processor to determine a first neutron dose based on the first treatment beam using the neutron dose detector at the first location, and to associate the first energy of the first treatment beam with the first number of soft errors experienced by the semiconductor-based device located at the second location, the first neutron dose, characteristics of the treatment room.

28. A system according to claim 27, wherein the soft errors comprise single-event upsets.

29. A system according to claim 27, wherein the beam source is to emit a second treatment beam associated with a second energy toward the neutron dose detector located at the first location,
wherein the semiconductor-based device located at the second location is to experience a second number of soft errors due, at least in part, to neutrons generated by the second treatment beam, and
wherein the processor is to determine a second neutron dose based on the second treatment beam using the neutron dose detector located at the first location, and to associate the second energy of the second treatment beam with the second number of soft errors experienced by the semiconductor-based device located at the second location and the second neutron dose.

30. A system according to claim 27, wherein the first treatment beam is associated with a first field size, and
wherein the processor is to associate the first energy of the first treatment beam and the first field size with the first number of soft errors and the first neutron dose.

31. A system according to claim 27, wherein the beam source is to emit a second treatment beam associated with the first energy toward a target,
wherein the semiconductor-based device is to experience a second number of soft errors due at least in part to neutrons generated by the second treatment beam; and
wherein the processor is to determine a second neutron dose at the target based on the association between the first energy, the first number of soft errors and the first neutron dose.

32. A system according to claim 31, wherein the target comprises an internal patient volume.

33. A system according to claim 32, wherein determination of the second neutron dose comprises:
determination that the second number of soft errors exceeds a threshold associated with a threshold neutron dose.

* * * * *